US005753503A

United States Patent [19]

Katinger et al.

[11] Patent Number: 5,753,503

[45] Date of Patent: May 19, 1998

[54] HUMAN MONOCLONAL ANTI-HIV-I-ANTIBODIES

[75] Inventors: Hermann W. D. Katinger, Heiligenstaedter Strasse 131-139/5/2/16, A-1190 Vienna, Austria; Ruediger von Baehr, Berlin, Germany; Alois A. Jungbauer, Vienna, Austria; Tomas Porstmann, Berlin, Germany; Franz J. Steindl, Vienna, Austria; Roland Grunow, Berlin, Germany

[73] Assignee: Hermann W. D. Katinger, Austria

[21] Appl. No.: 347,966

[22] Filed: Dec. 1, 1994

Related U.S. Application Data

[63] Continuation of Ser. No. 105,360, Aug. 10, 1993, abandoned, which is a continuation of Ser. No. 97,170, Jul. 23, 1993, abandoned, which is a continuation of Ser. No. 583,505, Sep. 17, 1990, abandoned, which is a division of Ser. No. 120,489, Nov. 13, 1987, abandoned.

[51] Int. Cl.$^6$ .............................. C12N 5/24; C07K 16/10; A61K 39/42
[52] U.S. Cl. .............................. 435/339.1; 424/142.1; 424/148.1; 435/70.21; 435/172.2; 530/388.15; 530/388.35; 530/391.1; 530/391.7
[58] Field of Search ..................... 424/9.34, 142.1, 424/160.1, 148.1, 188.1, 208.1; 435/5, 70.21, 172.2, 240.27, 339.1; 530/388.15, 388.35, 389.4, 391.1, 391.7

[56] References Cited

U.S. PATENT DOCUMENTS 5,087,557  2/1992  McClure ........................ 435/5

OTHER PUBLICATIONS

Fahey et al., "Status of Immune-based Therapies in HIV Infection and AIDS," *Clin. Exp. Immunol.* 88:1-5, 1992.
Fox, J.L., "No Winners Against AIDS," Bio/Technology 12:128, Feb. 1994.

*Primary Examiner*—Robert D. Budens
*Attorney, Agent, or Firm*—Bierman, Muserlian and Lucas

[57] ABSTRACT

The invention is directed to human monoclonal antibodies specific for the gp41 envelope protein of human immunodeficiency virus type 1 (HIV-1). Specifically disclosed are the human monoclonal antibodies produced by the cell lines 3D6 having ECACC Accession No. 87110301, 24G3 having ECACC Accession No. 90091702 and 25C2 having ECACC Accession No. 80120601.

7 Claims, 5 Drawing Sheets

HUMAN MONOCLONAL ANTI-HIV-I-ANTIBODIES

PRIOR APPLICATION

This application is a continuation of U.S. patent application Ser. No. 08/105,360 filed Aug. 10, 1993, now abandoned which is a continuation of U.S. patent application Ser. No. 08/097,170 filed Jul. 23, 1993, now abandoned which is a continuation of U.S. patent application Ser. No. 07/583,505 filed Sep. 17, 1990, now abandoned which is a division of U.S. patent application Ser. No. 07/120,489 filed Nov. 13, 1987, now abandoned.

This invention is in the field of immuhology and particularly concerns human monoclonal anti-HIV-I antibodies and immunochemicals made from these antibodies.

The production of human monoclonal antibodies (hu mAbs) may present a new source of antibodies to be used in immunotherapy against infections and other diseases.

The application of mAb of human origin instead of murine origin avoids the induction of antibody response in humans. The Fc-part of murine antibodies has to be removed prior to injection in humans to minimize antibody response against heterogenous administered proteins. Human monoclonal antibodies however present a part of the homologous proteins of human individuals.

In the sera of human immunodeficiency virus (HIV) infected men anti-virus antibodies could be detected over a certain period after infection with out any clinical manifestations of the acquired immunodeficiency syndrome (AIDS). At this state of active immune response high numbers of antigen-specific B cells were expected in the circulation. These B-cells were-used as fusion partners for the generation of human monoclonal anti-HIV antibodies.

We describe here:

the generation of human mAb to HIV antigens the substantial inhibition of growth of HIV-infected cells the preparation of immunotoxins conjugated with the described human anti-HIV-I mAb and and an A-chain toxin the selective killing of HIV-I infected cells with the immunotoxin the selective killing of HIV-I infected cells by antibody dependent cytotoxicity the selective prevention of cells from infection with the human monoclonal anti-IV-I antibody in vitro.

DETAILED DESCRIPTION OF THE INVENTION

Materials and Methods

Human anti-HIV-monoclonal antibodies (Hu anti-HIV-I mAb)

In the presently preferred embodiment of the invention the hu anti-HIV-I mAb used is of $IgG_1$ subclass produced according to known hybridization procedures described by R. Kennet et al. in "Monoclonal antibodies and functional cell lines; progress and applications". Plenum Press (New York), 1984. Samples of hybridoma 3D6, 24G3 and 25C2 were deposited in ECACC, Porton Down, Salisbury SP4 OJG, UK. The ECACC accession numbers for the deposited hybridomas are; 87110301 (3D6), 90091702 (24G3) and 89120601 (25C2).

Fusion

Fusion was performed in a described manner (Köhler et al., Europe Journal of Immunology 6 (1976) 292). Prior to cell fusion with PEG 1500 peripheral blood lymphocytes from HIV-I serum positive donors were washed three times with serum free cell culture medium. The cells were fused immediately or stimulated with 5 ng pokeweed mitogen (PWM) for three days prior to fusion. The cells were mixed at a ratio of 5:1 with HAT-sensitive fusion cells. The cells were fused with 42-% PEG (1500 Ferak, FRG) in the presence of 7.5% DMSO (Serva, FRG). Cells were cloned and subcloned by limiting dilution.

Screening of the Hybridomas

IgG and IgM isotypes were analyzed from the culture supernatant by a sandwich enzyme-linked immunosorbant assay (ELISA) with peroxidase conjugated anti-human IgG, IgM (heavy chain specific) antibodies in a known manner.

Screening for specific antibodies was performed by a sandwich ELISA using HIV in a concentration of 10 microgram/ml. The virus isolated from tissue culture was coated onto flat-bottom microtiter plates and the unbound material was washed out.

Immunoblotting

Immunoblot using HIV envelope proteins prepared from native virons: Purified virus was denatured and reduced with 2.5% SDS and 5.0% 2-mercaptoethanol at 90° C. for 5 min and applied to a 10% polyacrylamide slab gel. After separation protein bands were electio-transferred into a nitrocellulose sheet (Schleicher & Schull, FRG). After blocking the sheet with 5% dry milk, strips were cut and immersed in 5 ml 1:2 diluted culture supernatant. Bound antibodies were detected by reacting with anti-human IgG antibodies labeled with HRP and staining with diaminobenzidine containing 0.1% $NiCl_2$.

Immunoblot using HIV envelope proteins prepared from cloned material

SDS gel electrophoresis was performed according to Laemmli, Nature 227 (1970), 680–685. The electrophoretically separated envelope proteins derived from genetically engineered E. coli (L. H. Gosting, et al.: Journal of Clinical Microbiology 25 (1987), 845–848) were electro blotted to nitrocellulose. After blocking with 3% bovine serum albumin (BSA dissolved in PBS) the strips were immersed in samples diluted in PBS buffer (containing 0.1% Triton X-100, 1% BSA, 0.5% gelatine) overnight, washed 3 times and incubated with goat anti-human GAMMA-chain labeled with peroxidase.

Immunoblots using commercially available blot strips: Blot strips from Du Pont Lot 7044128 were used according to recommendations of the company.

Hybridization detection of human DNA $10^6$ cells of each cell line were spotted on a nitro-cellulose membrane. The hybridization probe was the $^{32}P$-labeled plasmid pBlur8 which contains a cloned Alu-sequence that is specific for human DNA and repeated about 300.000 times in the genome (Schmid et al., Science 216 (1982), 1065.

After prehybridization and hybridization overnight the membrane was washed 3× in 100 ml 2× SSC, 0.1% SDS for 5' at room temperature and 2× in 200 ml 1× SSC, 0.1% SDS for 30' at 60° C. and autoradiographed for 80 hours.

Immunofluorescence

Fixed HIV-I infected cells (H9 cells) were incubated with the hu anti-HIV mAb. Binding of the mAb was demonstrated by a second incubation after washing out unbound mAb with FITC labeled anti-human IgG.

Purification of the 3D6-antibodies

Purification was performed in a known manner. The clarified culture supernatant was desalted using gel filtration on a Sephadex G-25 column (Pharmacia) and further chromatographed on a CM-Sepharose fast flow column (Pharmacia). The eluate of the C-Sepharose fast flow column was concentrated by ultra-filtration and rechromatographed using Phenyl-superose (Pharmacia). The chromatographic steps were performed according to the recommendations of the Pharmacia company. Prior to loading the solution of the Phenyl-superose column the crude mAb solution was diluted by a 2M ammonium sulfate solution.

Preparation of ricin-A-chain toxin

Extraction of ricin from the castor bean

Ricin is extracted from castor beans (*Ricinus communis*) by known methods. Ricin is extracted either from grinded whole castor beans (*Ricinus communis*) or from castor bean cake, which is a by-product of castor bean processing. The castor bean cake is defatted by extraction 3 times with 5 volumes of (v/w) 40%–60% petroleum ether. The air-dried material is then extracted overnight in phosphate buffered saline (PBS; 0.15M NaCl, 0.01M phosphate, pH 7.2). The extract is cleared by filtration through a nylon gauze followed by centrifugation at 1500 g for 1 hour. The clear supernatant is precipitated at 4° C. with saturated ammonium sulfate. At a final end concentration of 60% ammonium sulfate the precipitate is collected and harvested by centrifugation (1500 g, 1 hour), redissolved in a minimum amount PBS and dialyzed against PBS until the extract is free from ammonium sulfate.

Cleavage of ricin into A- and B-chain

The affinity-purified and concentrated toxin is cleaved into A- and B-chain by a 5% 2-mercaptoethanol solution. The toxin is incubated at a concentration of 5 mg/ml in 0.1M Tris/HCL buffer pH 8.5 completed with 2-mercapto-ethanol (5% end concentration) and galactose (0.5M end concentration) overnight at room temperature, followed by 2–3 hours at 37° C. The toxin is transferred from the starting buffer (PBS) into the incubation buffer (Tris buffer) by gel chromatography on Sephadex G25 columns equilibrated with the incubation buffer.

After incubation the sample is applied to a DEAE-Sepharose fast flow column equilibrated with 0.1M Tris/HCl buffer pH 8.5. The column is washed with 0.1M Tris/HCl buffer pH 8.5 until all unbound material is eluted. The unbound material, essentially pure A-chain, is collected and passed down an asialo-fetuin-Sepharose 4B column to remove contaminating toxin. The asialo-fetuin-Sepharose 4B was prepared according to the recommendations of Pharmacia company.

The unbound material is collected and filter sterilized and stored at 4° C.

The DEAE-Sepharose fast flow is regenerated with a 0.1M Tris-HCl pH 8.5 containing 0.1M galactose and 1M NaCl.

Affinity chromatography

The clarified and dialyzed toxin extract is further purified by lectin affinity chromatography. The gel (Sepharose 4B, Pharmacia) is pretreated with 1M propionic acid at room temperature for at least 4 weeks to enhance its binding capacity for lectins.

The column chromatography should be operated at temperatures lower than 10° C. to optimize lectin binding.

The clarified and dialyzed extract is applied to a PBS-equilibrated acid pretreated Sepharose 4B column. After application of the sample, the column is washed with PBS until the UV-absorbance returns to the baseline.

The toxin is eluted together with other lectins with 100 mM galactose in PBS. This mixture is further separated by gel chromatography on Sephacryl S200HR. The sample volume should not exceed 3–4% of the bed total volume. The toxin is resolved completely from the other lectins under these conditions. The toxin recovered from the affinity column is concentrated to 10 mg/ml by ultrafiltration (Milipore PTGC membrane) prior to application on Sephacryl S200 HR column.

The toxin peak was collected and filter sterilized. The sterile toxin solution was stored deep frozen at −30° C. until cleavage into A and B-chain.

Determination of the isoelectric point

The isoelectric point of the hu anti-HIV-I mAb was determined by a described method. Pharmalytes were used as carrier ampholytes. The whole procedure was carried out according to the recommendation of the Pharmacia company (booklet: Isoelectric focussing, Pharmacia fine chemicals).

Determination of subclass and light chains

Light chains and subclass were determined by ELISA. Specific anti-human KAPPA-CHAIN antibodies labeled with alkaline phosphatase or specific anti-human $G_1$, $G_2$, $G_3$ and $G_4$ antibodies labeled with peroxidase were used.

Quality control of ricin A-chain

Quality control tests are performed on the purified ricin-A chain. Gradient SDS-polyacrylamide gel electrophoresis under reduced conditions shows the absence of any contaminating material. Only one band at 33 and one at 30 kilo-dalton respectively can be detected.

Conjugation of A-chain toxin with monoclonal antibody 5 mg of purified monoclonal antibody (1–2 mg/ml in PBS) were reacted with a 10-fold molar excess of SPDP (Pharmacia), dissolved at 1 mg/ml in dimethylformamide for 30 min at room temperature. PDP-substituted antibody was desalted by gel filtration using Sephadex G-25. The protein peak fraction continuously determined at 280 nm was collected and placed on ice. Five mg of ricin A-chain were reduced with 5 mM DDT for 1 hour at room temperature and desalted on a column of Sephadex G-25. The column was equilibrated with PBS. The protein peak fraction was collected and immediately mixed with the cold PDP-substituted antibody. The mixture was rocked for 1 hour at 4° C. and then diafiltrated at 4° C. against 0.01M sodium phosphate buffer containing 2.0M sodium chloride. The bulk of the unconjugated A-chain was separated from the immunotoxin by gel chromatography on Sephacryl S200-HR. The column was equilibrated in 0.02M sodium phosphate containing 3M sodium chloride.

The fraction of the first peak which contained the immunotoxin was pooled and affinity-purified on an anti-human IgG-Sepharose 4B. The immunotoxin was eluted from the affinity column with 3.5M magnesium chloride and extensively dialyzed against sodium chloride and against PBS.

Immunotoxins (0.2–2 mg/ml) were concentrated by ultrafiltration using PTGC membranes to end concentration necessary for testing. The final preparation was sterile filtered and stored in aliquots at −20° C. The immunotoxins were analyzed by SDS-PAGE under both reducing and non-reducing conditions. The substitution of the immunotoxin was determined by radioimmunoassay. An average substitution of 1–2 moles A-chain per mole antibody was observed.

Competitive EIA

Purified hu anti-HIV mAb were conjugated with peroxidase by a known method according to M. B. Wilson and P.

K. Nakane (1978) in "Immunofluorescence and related techniques" ed. W. Knapp et al. Elsevier Netherlands.

A dilution series of hu anti-HIV mAb (in PBS with 1% BSA and 0.1% Triton X-100) was dispensed in flat-bottomed microtiter wells coated with purified HIV envelope proteins incubated overnight at 4° C. After washing out unbound material the bound conjugate was determined by reaction with 1,4 phenylenediamine. The developed colour was measured at 492 nm. As a calibration curve the optical density was plotted versus dilution. The dilution of the half saturation is calculated from this calibration curve. Hu anti-HIV mAb at a dilution corresponding to the half maximum saturation was mixed with sera from patients suffering from AIDS or with sera from probands who were sero positive as determined by a conventional screening (ELISA) followed by a confirmation test (westernblot). The mixture of the conjugate (at half maximal dilution) and the serum. from the probands were incubated in HIV envelope protein-coated microtiter wells, washed and stained.

The optical density of these samples is compared to the anti HIV mAb at half maximum saturation. A value below the half maximum saturation indicates a competition between the human sera and the human monoclonal anti-HIV antibody.

HIV-I neutralizing activity

The assay for neutralizing activity of the hu anti-HIV mAb was performed according to a known method (J. Virology 61 (1987) , 2024–2428), Nature 316 (1985), 72–74; Biotechnology 5 (1987) 940–946).

An HIV-I dose equivalent to twenty times the amount to cause infection in 50% inoculated cultures on day 12 (20× $TCID_{50}$) was used to infect the H9 cell line. Cells were collected 3, 6, 9 and 12 days after virus inoculation and the percentage of infection was determined by immunofluorescence. 100% infection was observed between day 6 and 9.

The neutralizing effect was also tested in the presence of the monoclonal antibody at variable dilutions.

Cytotoxicity tests

The test cell line used in the cytotoxicity tests were HIV-I infected H9 cells prepared as described above under "HIV-I neutralizing activity". Uninfected H9 cells were used as negative control. Cells harvested after a period of 6–9 days after virus inoculation were suspended in 1 ml medium.

Various dilutions of the hu mAb-toxin conjugate were added to the infected cells and the negative control. After incubation for 24 hours at 370° C. cells were washed with PBS and methionine-free medium supplemented with $^{35}S$-methionine was added. Cells were incubated for 2 hours at 37° C., then the medium was removed by centrifugation and the cells transferred to a glassfiber filter and washed three times with 10% trichloroacetic acid, containing 1 mg/ml methionine. The cells were air dried on the filter and then transferred into a scintillation fluid. Radioactivity was counted in a scintillation counter. Cytotoxicity was expressed as the tissue culture inhibitory dose of the conjugate that resulted in 50% of the protein synthesis of the untreated control $(TCID)_{50}$.

EXPERIMENTAL RESULTS

A variety of experiments are shown to serve as examples for illustrating the present invention and its utilization in the following embodiments.

The human origin, the biochemical properties, the immunochemical characterization, the in vitro and in vivo behaviour are demonstrated by representative results.

Generation of clones and human origin of the monoclonal antibodies

A variety of clones was obtained by the fusion of peripheral blood lymphocytes and the fusion cell line. The specificity of 6 hybridomas is shown in Table I.

TABLE I

Characterization of 6 hybridomas

| Hybridoma No. | Specificity of mAb test by immunoblotting | isotype and subclass | light chain |
|---|---|---|---|
| 3D6 | gp41 | G1 | KAPPA |
| 3D9 | gp41 | G | n.d. |
| 24G3 | gp41 | G | n.d. |
| 25C2 | gp41 | G | n.d. | n.d. = not determined

Figure 1A:
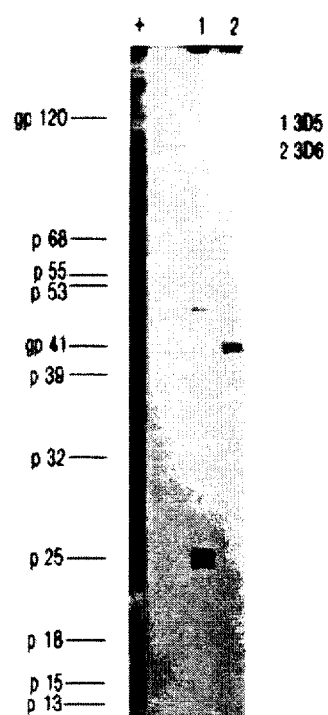
FIG. 1A is an immunoblot of the human mAb produced by Hybridoma No. 3D6.
Figure 1B:
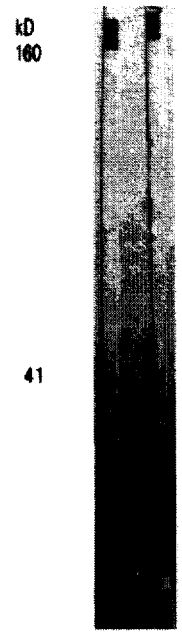
FIG. 1B is an immunoblot of the human anti-HIV mAb produced by Hybridoma 3D6.
Figure 1C:
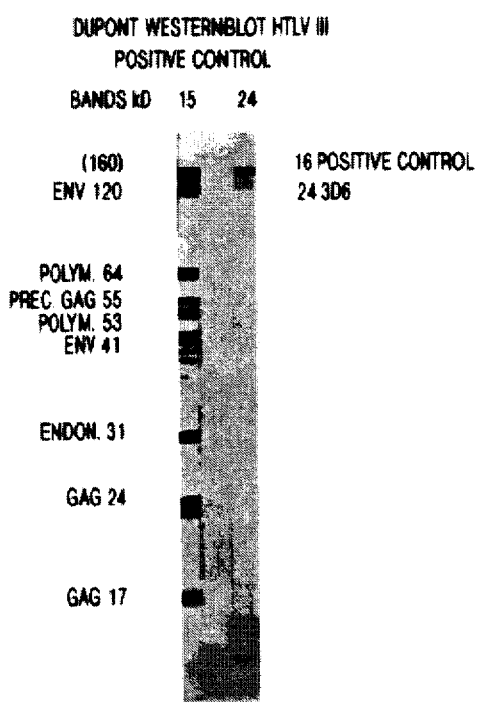
FIG. 1C is an immunoblot of the human anti-HIV mAb produced by Hybridoma 3DG.

The hu anti-HIV-I mAb produced by hybridoma cell line 3D6 is used as an example to illustrate the present invention. Immunoblots of the 3D6 antibody are shown in FIGS. 1A, 1B and 1C. In FIG. 1A, HIV envelope proteins were prepared from native virons by SDS and 2-mercaptoethanol treatment. In FIG 1B, HIV envelope proteins were prepared from genetically engineered E. coli (according to a known procedures L. H. Gosting et al: Journal of Clinical Microbiology 25 (1987), 856–848). In FIG. 1C, a commercially available blot strip (Du Pont Lot.: 70 44 128) was used.

Figure 2:
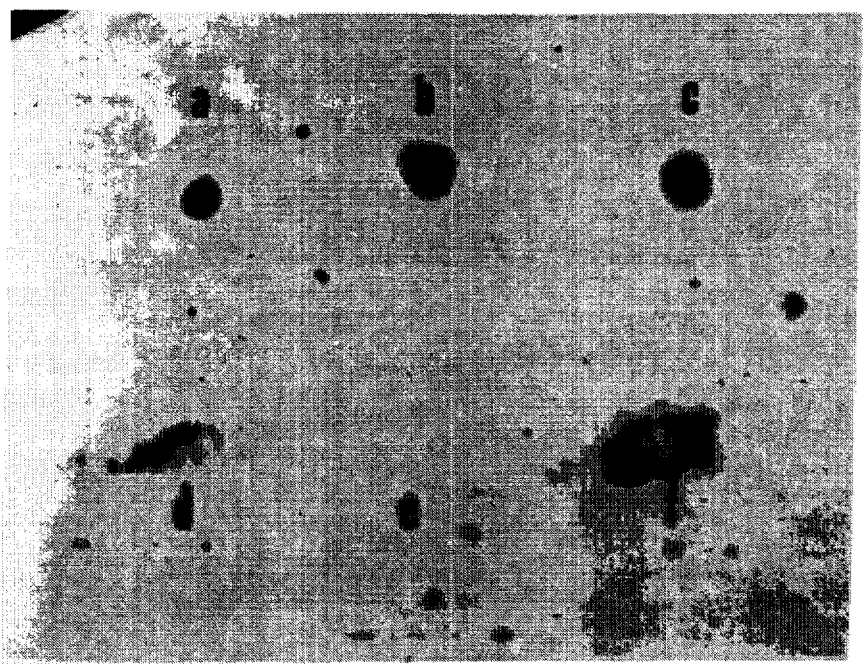
FIG. 2 illustrates the detection of human DNA by hybridization.

The human origin of the monoclonal antibody is shown by the hybridization of $^{32}P$-labeled plasmid pBlur8. Autoradiographs are shown in FIG. 2 with the DNA of the hybridoma cells. Also the reaction with anti-human IgG and human IgM antisera and the more specific sera for subclass determination verifies the human origin of the monoclonal antibodies.

In FIG. 2, letters a) through f) mark the different cell lines tested: a) 3D5; b) 3D9; c) 24G3; d) BJA-B (human lymphoid cell line, positive control; e) P3X63Ag/653 (murine myeloma, negative control; f) BUBTT (human bladder carcinoma, positive control.

Biochemical properties and immunochmical characterization of the antibody.

The isotype of the monoclonal antibody produced by hybridoma 3D6 is G. The subclass determined by ELISA is G1. The isoelectric point, determined by isoelectric focussing using the Pharmacia system is in the range of pH 8.6.

Immunofluoreacence

Figure 3A:
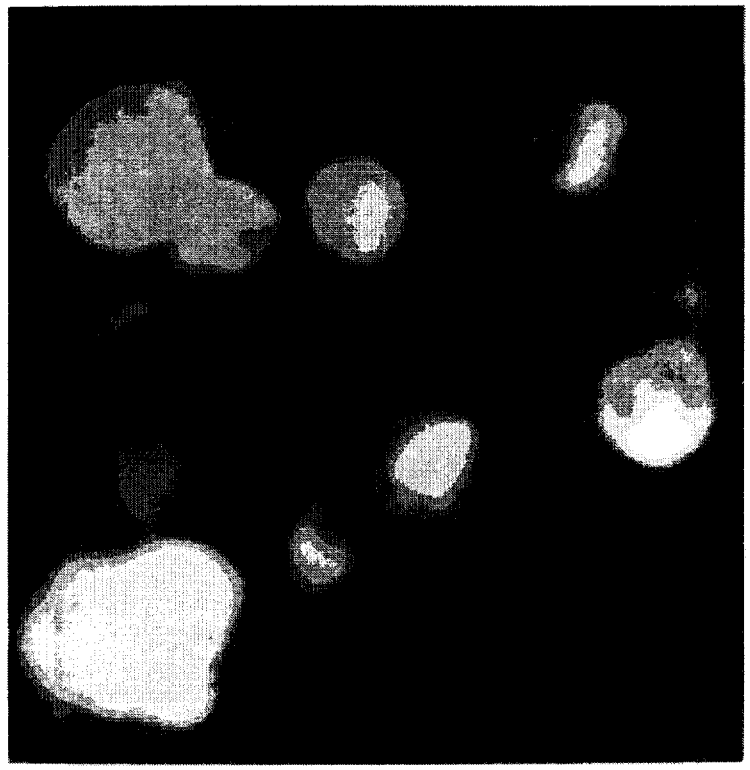
FIGS. 3A–3B show the specific immunofluorescence of fixed HIV-I infected H9 cells.
Figure 3B:
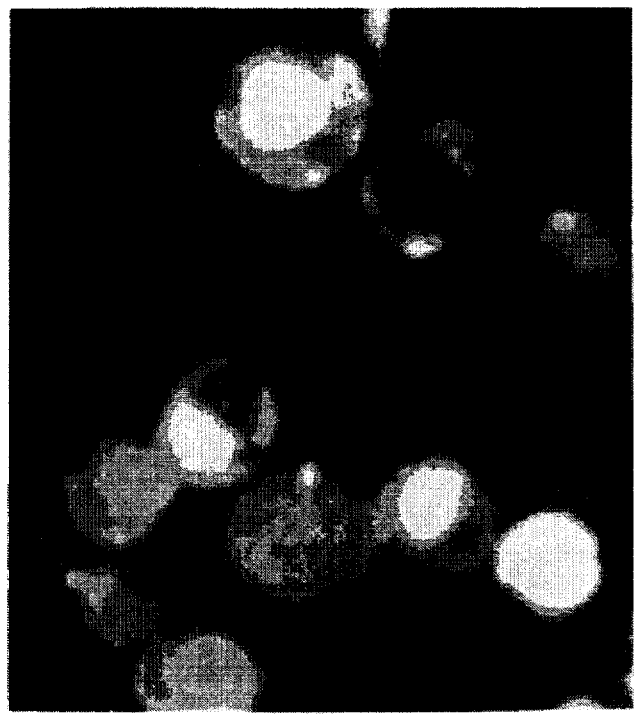

Fixed HIV infected cells were incubated with the 3D6 antibody. Specific fluorescence caused by the market conjugate anti-human IgG-FITC is shown in FIG. 3. The HIV-I infected H9 cells were imaged with a sandwich of 3D6 antibody and anti-human IgG conjugated with FITC. Clones 3D6 and 3D5 are shown.

In vitro behaviour of the monoclonal antibodies and related immunotoxins.

Neutralizing activity

Figure 4:
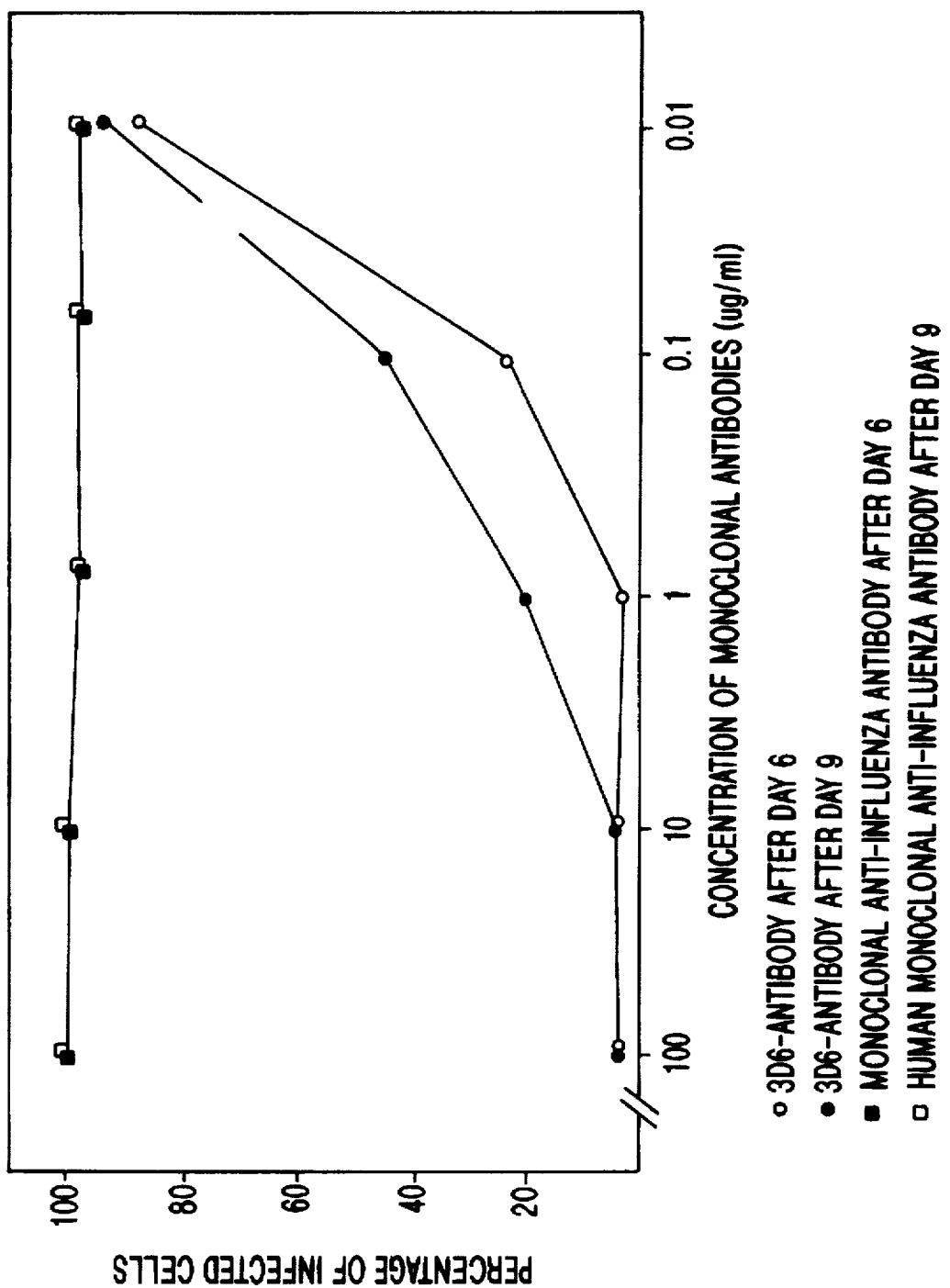
FIG. 4 is a graph showing neutralizing activity of 3D6 antibody.

In the presence of up to 1 ug/ml 3D6 antibody H9 cells could not be infected by 20 times TCID50 of HIV virons. The neutralizing activity of antibody 3D6, expressed as percent of infected cells, is shown in FIG. 4. Infected cells were shown by immunofluorescence using the 3D6 antibody. 9 days after inoculation with 20 times $TCID_{50}$ of HIV-I virus 0.1 ug/ml of antibody 3D6 could prevent HIV infection in H9 cells.

Cytotoxicity

The monoclonal antibody 3D6 covalently linked with the ricin A-chain was used to demonstrate the cytotoxicity of the antibody. The cytotoxicity was measured by $^{35}$S-methionine uptake.

Figure 5:
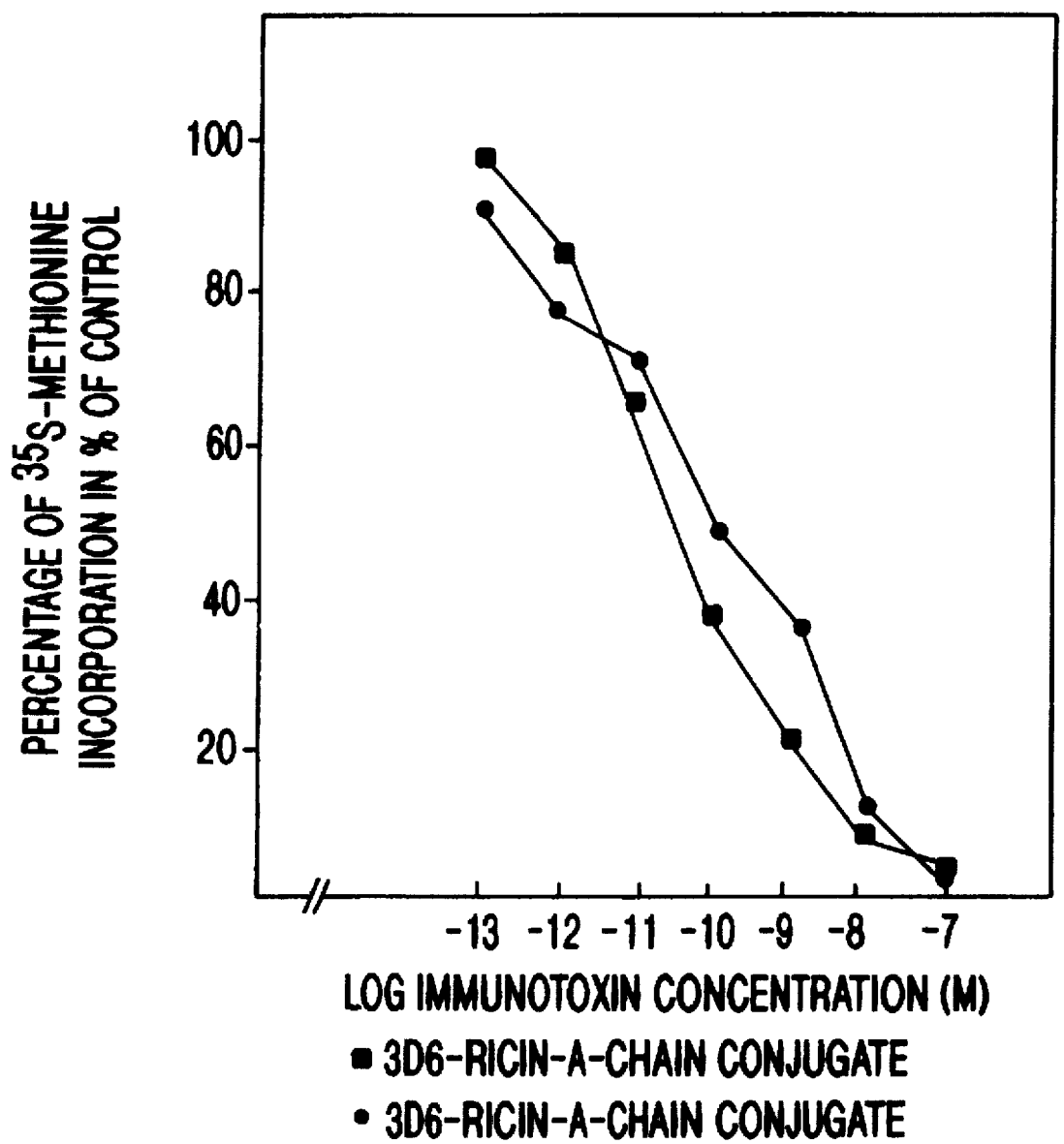
FIG. 5 shows the inhibition of protein synthesis as a measure of cytotoxicity.

The immunotoxin consisting of a conjugate between 3D6 antibody and ricin A-chain, prepared as described above under "Materials and methods" specifically killed HIV-I infected H9 cells. The inhibition of protein synthesis determined by $^{35}$S-methionine uptake was taken as a measure for cytotoxicity. The $^{35}$S-methionine uptake is expressed in percent of the control (FIG. 5).

On the basis of assuming a molecular weight of 180000 dalton the molar concentration of the inunotoxin was calculated. The $TCID_{50}$ of the immunotoxin (3D6-ricin-A-chain) is less than 10 mM.

Comparison of the hu anti-HIV-mAb with naturally occurring antibodies from seropositives and patients suffering from AIDS or pre-AIDS.

A competitive EIA (Enzyme immunoassay) was chosen to compare the claimed monoclonal antibodies with naturally occurring antibodies in men after a HIV infection.

The 3D6 monoclonal antibody was conjugated with peroxidase and the dilution of the half maximum saturation was determined. The 3D6 antibody at a dilution of half maximum saturation was mixed with different sera from seropositives without clinical manifestation of AIDS and with sera from patients suffering from AIDS or pre-AIDS in a ratio of 1:1. The competition between the 3D6 antibody and the naturally occurring antibodies in blood are expressed in percent% of the half maximum saturation.

The half maximum saturation with the 3D6 antibody alone is taken as 100%. Table II shows the values from competitive EIA using a 3D6-antibody peroxidase conjugate and different sera.

TABLE II

Comparison between 3D6 antibody and sera from seropositives and patterns suffering from AIDS or pre-AIDS

| Patient or propand No. | % of half maximum saturation | Clinical manifestation of AIDS (1) in pre-AIDS (2) seropositive proband (3) |
|---|---|---|
| 1 | 96 | 3 |
| 2 | 91 | 3 |
| 3 | 84 | 3 |
| 4 | 88 | 3 |
| 5 | 92 | 3 |
| 6 | 50 | 3 |
| 7 | 94 | 3 |
| 8 | 98 | 3 |
| 9 | 96 | 3 |
| 10 | 85 | 2 |
| 11 | 85 | 3 |
| 12 | 88 | 3 |
| 13 | 95 | 2 |
| 14 | 97 | 2 |
| 15 | 88 | 3 |
| 16 | 88 | 3 |
| 17 | 94 | 3 |
| 18 | 92 | 3 |
| 19 | 96 | 1 |
| 20 | 25 | 3 |
| 21 | 96 | 3 |
| 22 | 94 | 3 |
| 23 | 94 | 3 |
| 24 | 90 | 1 |
| 25 | 82 | 2 |
| 26 | 88 | 3 |
| 27 | 94 | 3 |
| 29 | 94 | 3 |
| 30 | 96 | 1 |
| 31 | 82 | 3 |
| 32 | 86 | 2 |
| 33 | 80 | 3 |
| 34 | 48 | 3 |
| 35 | 84 | 3 |
| 36 | 92 | 3 |
| 37 | 94 | 2 |
| 38 | 98 | 3 |
| 39 | 98 | 3 |
| 40 | 96 | 3 |
| 41 | 88 | 3 |
| 42 | 90 | 3 |
| 43 | 94 | 2 |
| 44 | 92 | 3 |
| 45 | 86 | 3 |
| 46 | 84 | 3 |
| 47 | 92 | 1 |
| 48 | 94 | 3 |
| 49 | 87 | 3 |
| 50 | 96 | 2 |

All sera were HIV seropositive determined by the conventional screening assay and the seropositivity was confirmed by westernblots. The 3D6 antibody recognizes the same epitopes as naturally occurring antibodies in the blood after HIV infection.

In all cases (Table II, probands 1–50) a competition could be observed.

We claim:

1. A human monoclonal antibody capable of selectively binding to gp41 of envelope protein gp2160 of HIV-1 wherein the said antibody is produced by a cell line selected from the group consisting of 3D6 having ECACC accession No. 87110301, 24G3 having ECACC accession No. 90091702 and 25C2 having ECACC accession No. 89120601.

2. The antibody according to claim 1 wherein said antibody is conjugated with a ligand.

3. The antibody according to claim 1 wherein the ligand is the A-chain of ricin.

4. A hybridoma cell line producing a human monoclonal antibody according to claim 1.

5. The cell line of claim 4 wherein the said cell line is selected from the group consisting of cell lines 3D6 having ECACC accession No. 87110301, 24G3 having ECACC accession No. 90091702 and 25C2 having ECACC accession No. 89120601.

6. The antibody according to claim 1, wherein said antibody is of an IgG isotype.

7. A human monoclonal antibody having all the identifying characteristics of an antibody produced by a cell line selected from the group consisting of cell line 3D6 having ECACC Accession No. 87110301, cell line 24G3 having ECACC Accession No. 90091702 and cell line 25C2 having ECACC Accession No. 80120601.

* * * * *